United States Patent [19]
Liebetruth

[11] Patent Number: 5,377,252
[45] Date of Patent: Dec. 27, 1994

[54] COMPUTER TOMOGRAPHY APPARATUS WITH BEAM THICKNESS ADJUSTMENT

[75] Inventor: Reiner Liebetruth, Erlangen, Germany

[73] Assignee: Siemens Aktiengesellschaft, Munich, Germany

[21] Appl. No.: 164,721

[22] Filed: Dec. 10, 1993

[30] Foreign Application Priority Data

Feb. 9, 1993 [DE] Germany ............... 4303748

[51] Int. Cl.$^5$ ............................... G21K 1/04
[52] U.S. Cl. .................... 378/151; 378/147; 378/150; 378/4
[58] Field of Search ............ 378/145, 146, 147, 148, 378/149, 150, 151, 152, 159, 4, 14, 19, 16

[56] References Cited

U.S. PATENT DOCUMENTS 5,228,070  7/1993  Mattson ................. 378/146
5,235,627  8/1993  Takagi .................... 378/145

FOREIGN PATENT DOCUMENTS 3828542  12/1989  Germany .

OTHER PUBLICATIONS

"Performance Issues in Computed Tomography Specifications" Burstein, Materials Evaluation, vol. 48, May 1980 (pp. 579–593).

Primary Examiner—David P. Porta
Assistant Examiner—Don Wong
Attorney, Agent, or Firm—Hill, Steadman & Simpson

[57] ABSTRACT

In a computer tomography apparatus having an x-ray radiator and a radiation detector rotatable on a frame around an examination subject, so that an x-ray beam is also rotated around the subject, the plates of a primary radiation diaphragm are controlled so that the thickness of the x-ray beam, measured in a direction perpendicular to its propagation direction, is varied dependent on the rotational angle of the x-ray beam. During examination of subjects having a highly elliptical cross-section, image artifacts are avoided because the beam thickness is varied so that more quanta reach the detector in the angular range wherein the most pronounced radiation attenuation occurs, thereby reducing the noise in the detector signal.

4 Claims, 1 Drawing Sheet

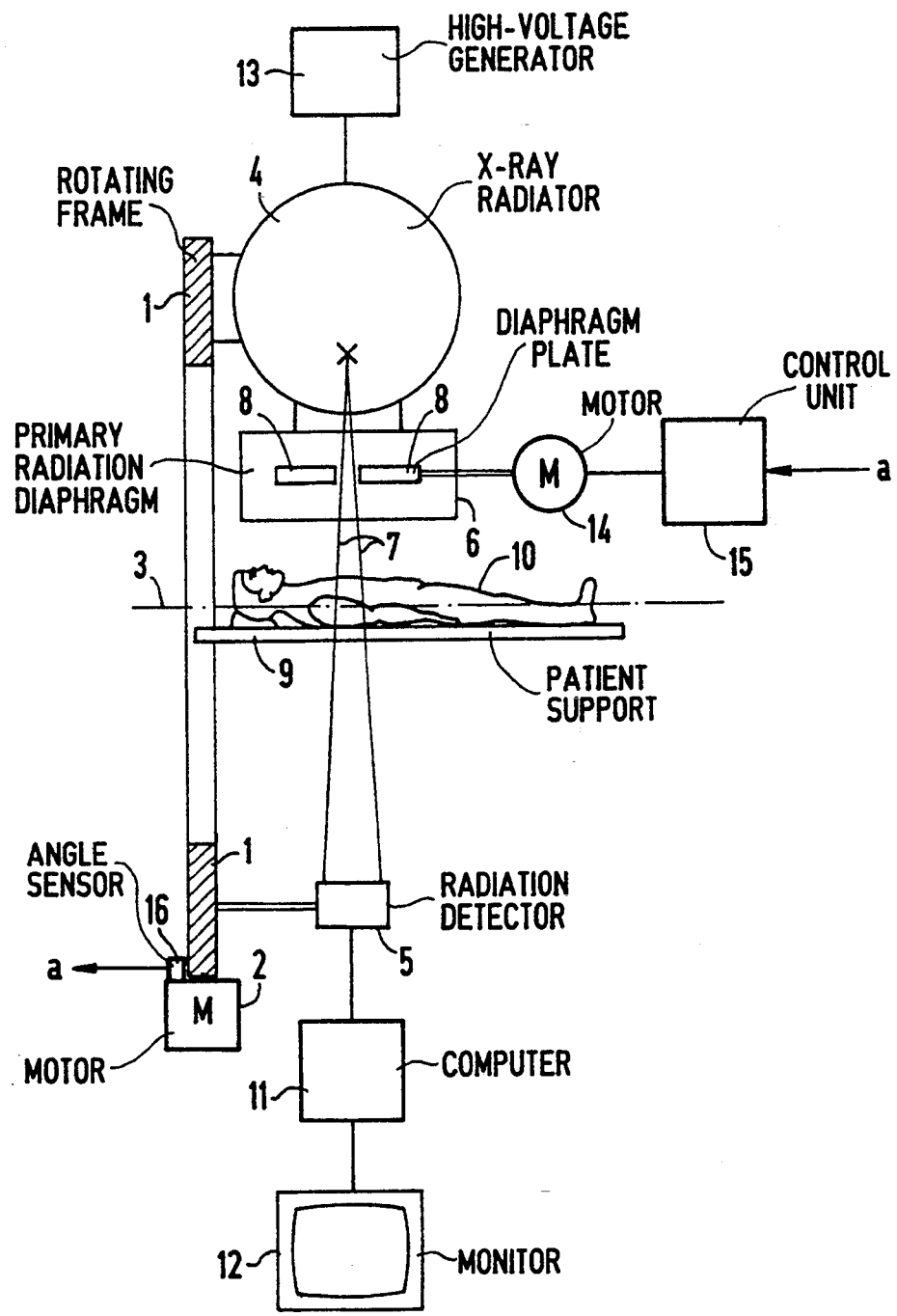

COMPUTER TOMOGRAPHY APPARATUS WITH BEAM THICKNESS ADJUSTMENT

BACKGROUND OF THE INVENTION

1. Field of the Invention

The present invention is directed to a computer tomography apparatus of the type having an x-ray source which emits a fan-shaped x-ray beam, shaped by a primary radiation diaphragm, which is rotated around a measurement field so as to transirradiate a measurement field from different directions, the attenuated radiation being incident on a radiation detector which converts the incident radiation into electrical signals which are supplied to a computer for generating images.

2. Description of the Prior Art

In known computer tomography systems of the above type, for example in computer tomography systems of the third generation having an arcuate detector composed of a row of detector elements which is rotated around the measurement field together with the x-ray source, the thickness of the x-ray beam (i.e., the extent of the x-ray beam in a direction perpendicular to the fan plane and perpendicular to the direction of radiation propagation) is constant during the scanning, i.e., during the rotation. When subjects are examined which have a highly elliptical cross section, for example when scanning the shoulder or hip region of a human patient, measured values are obtained which contain a large amount of noise, which leads to disturbing horizontal artifacts in the image which is reconstructed from those measured values by the computer. These image artifacts are caused by the low number of quanta which are able to reach the detector at certain of the angular projections. In known systems, these artifacts are attenuated by means of appropriate computational algorithms. It is also known to minimize such artifacts by regulating the high-voltage supply (generator power). The extent to which the generator power can be modified, however, is very small.

SUMMARY OF THE INVENTION

It is an object of the present invention to provide a computer tomography apparatus of the type having an x-ray source which rotates around a measurement field wherein image disturbances of the type described above are substantially eliminated without the use of computational algorithms and without the necessity of regulating the generator power.

The above object is achieved in accordance with the principles of the present invention in a method and apparatus wherein thickness of the x-ray beam perpendicularly to the fan plane is varied during rotation of the x-ray beam around the measurement field. In one embodiment of the invention, the thickness variation is accomplished by providing an angular sensor which generates a signal corresponding to the angle at which the x-ray beam currently resides relative to the measurement field, this signal being used to control the position of the plates of primary radiation diaphragm. The opening between the plates, and thus the thickness of the x-ray beam, are varied dependent on the amount of attenuation of the beam which takes place at the respective angular positions, this amount of attenuation being known (or predictable) based on the cross section of the subject being examined.

In the computer tomography apparatus of the invention, therefore, the generator power is maintained constant throughout the rotation of the x-ray beam, but the slice thickness is varied by means of varying the aperture of the primary radiation diaphragm. When conducting an exposure having a nominal slice thickness of, for example, 3 mm, the diaphragm aperture, and thus the slice thickness, are enlarged in a prescribed annular range wherein an especially pronounced attenuation of the x-rays occurs. More quanta thus reach the radiation detector, so that the noise in the detector signal is reduced.

DESCRIPTION OF THE DRAWINGS

The single FIGURE is a schematic diagram of a computer tomography apparatus with beam thickness adjustment, constructed in accordance with the principles of the present invention and operating in accordance with the principles of the method of the present invention.

DESCRIPTION OF THE PREFERRED EMBODIMENTS

The computer tomography apparatus constructed in accordance with the principles of the present invention shown in the drawing includes a rotating frame 1 which is rotatable around a system axis 3 by a motor 2. The rotating frame 1 carries an x-ray radiator 4 and a radiation detector 5. The x-ray radiator 4 generates a fan-shaped beam 7 in a plane lying perpendicularly to the plane of the drawing. A primary radiation diaphragm 6, having adjustable diaphragm plates 8, is disposed in the path of the x-ray beam 7 for gating the x-ray beam 7. The thickness of the x-ray beam 7, i.e., its extent in a direction perpendicular to the plane of the fan beam 7, is thereby defined by the position of the adjustable diaphragm plates 8.

The x-ray beam 7 penetrates a measurement field in which a patient support 9 having a patient 10 thereon are disposed.

The radiation detector 5, which is composed of a row of detector elements, converts the x-rays incident thereon into corresponding electrical signals, which are supplied to a computer 11 which constructs an image of the patient 10 therefrom. The image is displayed on a monitor 12. The x-ray radiator 4 is fed by a high-voltage generator 13.

Transverse slice images, for example, of selected slices of the patient 10 can be produced with the computer tomography apparatus shown in the drawing. For this purpose, the rotating frame 1 is rotated through 360° for conducting a scan of a slice.

During such a can, the thickness of the x-ray beam 7 is varied in accordance with the principles of the present invention. This is accomplished in the embodiment shown in the drawing by a motor 14 which operates the diaphragm plates 8 so as to adjust the aperture formed by the plates 8, which in turn determines the thickness of the x-ray beam 7. The motor is operated by a control unit 15 which receives a signal "a" from an angle sensor 16. The angle sensor 16 is positioned to generate a signal corresponding to the current angular position of the rotating frame 1, the signal "a" thus also identifying the current angular position of the x-ray beam 7. If a slice of the examination subject 10 is to be examined which has a highly elliptical cross section, for example, the x-ray beam 7 will have to propagate through the larger distance within the subject when the central ray of the fan-shaped beam 7 is within a range in either side of the major axis of the ellipse of the elliptical cross section than will be case when the central ray of the x-ray beam 7 is within a range on either side of the minor axis of the ellipse. As a consequence, the radiation of the x-ray beam 7 will be more attenuated when the central ray is within a first angular range than will be the case when the central ray is in a different angular range. By monitoring the angular position of the rotating frame 1, and thus the angular position of the x-ray beam 7, using the angle sensor 16, the control unit 15, dependent on the signal "a" operates the motor 14 to adjust the aperture of the diaphragm plates 8 accordingly, so that the x-ray beam 7 can be made thicker as needed during the course of a complete rotation. The radiation detector 5 thereby receives more quanta in those angular ranges wherein the beam is made thicker, thereby reducing the noise in the resulting signal. Reduction of the noise substantially reduces, or completely eliminates, the aforementioned image artifacts caused by signal noise.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computer tomography apparatus comprising:
an x-ray source which emits a fan-shaped x-ray beam in a beam plane, said x-ray beam having a thickness in a direction perpendicular to said beam plane;
means for rotating said x-ray source and said x-ray beam around a measurement field for irradiating a subject in said measurement field from different directions;
detector means disposed for detecting radiation from said x-ray beam after passing through said measurement field and for converting said radiation into corresponding electrical signals;
computer means for generating an image of said subject from said electrical signals;
a primary radiation diaphragm disposed in the path of said fan-shaped x-ray beam before said measurement field, said primary radiation diaphragm having adjustable diaphragm plates setting an aperture which defines said thickness of said x-ray beam; and means for adjusting said aperture of said diaphragm plates during rotation of said x-ray beam, including angle sensor means for generating a control signal dependent on the angle of said x-ray beam, and a motor for moving said diaphragm plates to set said aperture, said motor being supplied with said control signal from said angle sensor means for setting said aperture dependent on said angle of said x-ray beam.

2. A computer tomography apparatus as claimed in claim 1 wherein said subject has an elliptical cross section having a major axis, and wherein said means for modifying the thickness of said x-ray beam during rotation of said x-ray beam comprises means for increasing the thickness of said x-ray beam when a central ray of said x-ray beam is within a predetermined range on either side of said major axis.

3. A method for operating a computer tomography apparatus comprising the steps of:
generating a fan-shaped x-ray beam in a beam plane and having a thickness in a direction perpendicular to said beam plane;
rotating said x-ray beam around a measurement field in which an examination subject is disposed for irradiating said subject from different directions;
detecting radiation passing through said measurement field and converting the detected radiation into electrical signals;
generating an image of said examination subject from said electrical signals; and
modifying the thickness of said x-ray beam during rotation of said x-ray beam around said subject by gating said x-ray beam which a primary radiation diaphragm having adjustable diaphragm plates with set an aperture defining said thickness, sensing an angle of said x-ray beam relative to said subject, and moving said diaphragm plates during rotation of said x-ray beam dependent on said angle.

4. A method as claimed in claim 3 wherein said examination subject has an elliptical cross section having a major axis, and wherein the step of modifying the thickness of said x-ray beam during rotation of said x-ray beam is further defined by increasing the thickness of said x-ray beam when a central ray of said x-ray beam is within a predetermined range on either side of said major axis.

* * * * *